(12) United States Patent
Wozencroft (10) Patent No.: US 11,382,767 B2
(45) Date of Patent: Jul. 12, 2022

(54) HIP CUP ALIGNMENT GUIDE (71) Applicant: Embody Orthopaedic Limited, London (GB)

(72) Inventor: Robert Michael Wozencroft, Epsom (GB)

(73) Assignee: Embody Orthopaedic Limited, London (GB)

( * ) Notice: Subject to any disclaimer, the term of this patent is extended or adjusted under 35 U.S.C. 154(b) by 0 days.

(21) Appl. No.: 16/763,868

(22) PCT Filed: Dec. 8, 2018

(86) PCT No.: PCT/EP2018/084070
§ 371 (c)(1),
(2) Date: May 13, 2020

(87) PCT Pub. No.: WO2019/110840
PCT Pub. Date: Jun. 13, 2019

(65) Prior Publication Data
US 2020/0345514 A1 Nov. 5, 2020

(30) Foreign Application Priority Data

Dec. 8, 2017 (GB) .................................. 1720515

(51) Int. Cl.
*A61F 2/46* (2006.01)
*A61B 17/17* (2006.01)
(Continued)

(52) U.S. Cl.
CPC ........ *A61F 2/4609* (2013.01); *A61B 17/1746* (2013.01); *A61F 2/30771* (2013.01);
(Continued)

(58) Field of Classification Search
CPC ............... A61F 2/4609; A61B 17/1746; A61B 2017/568
See application file for complete search history.

(56) References Cited

U.S. PATENT DOCUMENTS

| 7,396,357 | B2 * | 7/2008 | Tornier | ................. | A61F 2/4609 606/91 |
| 8,128,631 | B2 * | 3/2012 | Johnson | ................. | A61F 2/4609 606/90 |

(Continued)

FOREIGN PATENT DOCUMENTS

| WO | WO-2017077341 A1 | 5/2017 |
| WO | WO-2019110840 A1 | 6/2019 |

OTHER PUBLICATIONS

"International Application Serial No. PCT/EP2018/084070, International Search Report dataed Mar. 19, 2019", 6 pgs.

(Continued)

*Primary Examiner* — Anu Ramana
(74) *Attorney, Agent, or Firm* — Schwegman Lundberg & Woessner, P.A.

(57) ABSTRACT

An acetabular cup guide can include a distal end (11) shaped to allow removable connection to a surgical instrument (16), a proximal end including one or more contact surfaces (4, 5) shaped to conform to an acetabulum, and a central proximal-distal axis extending through the acetabular cup guide. At least one of the one or more contact surfaces can be configured such that it is deflectable towards the central proximal-distal axis in order to reduce an axial cross-section of the acetabular cup guide.

17 Claims, 10 Drawing Sheets

(51) Int. Cl.
*A61F 2/30* (2006.01)
*A61B 17/56* (2006.01)

(52) U.S. Cl.
CPC .................. *A61B 2017/568* (2013.01); *A61F 2002/30841* (2013.01)

(56) References Cited

U.S. PATENT DOCUMENTS

| | | |
|---|---|---|
| 9,011,456 B2 * | 4/2015 | Ranawat ................ A61B 34/10 606/91 |
| 2004/0215200 A1 | 10/2004 | Tornier et al. |
| 2011/0092979 A1 | 4/2011 | Bartelme et al. |
| 2015/0190151 A1 | 7/2015 | Budhabhatti et al. |
| 2016/0228133 A1 | 8/2016 | Meridew et al. |

OTHER PUBLICATIONS

"International Application Serial No. PCT/EP2018/084070, Written Opinion dated Mar. 19, 2019", 7 pgs.
"United Kingdom Application Serial No. 1720515.4, Combined Search and Examination Report dated May 8, 2018", 6 pgs.
"United Kingdom Application Serial No. 1720515.4, Subsequent Examination Report dated Mar. 31, 2020", 2 pgs.
"European Application Serial No. 18816032.9, Response to Communication pursuant to Rules 161(1) and 162 EPC filed Jan. 25, 2021", 16 pgs.
"International Application Serial No. PCT/EP2018/084070, International Preliminary Report on Patentability dated Jun. 18, 2020", 9 pgs.
"United Kingdom Application Serial No. 1720515.4, Intent to Grant Under Section 18(4) dated Jul. 21, 2020", 2 pgs.

* cited by examiner

HIP CUP ALIGNMENT GUIDE

This application is a U.S. National Stage Application under 35 U.S.C. 371 from International Application Serial No. PCT/EP2018/084070, filed on Dec. 8, 2018, and published as WO2019/110840 A1 on Jun. 13, 2019, which claims priority to United Kingdom Application No. 1720515.4, filed on Dec. 8, 2017, the benefit of priority of each of which is claimed hereby, and each of which are incorporated by reference herein in its entirety.

BACKGROUND

In hip replacement surgery, to regain natural range of motion and to ensure the bearing functions well over the patient's lifetime, it is very important to position and orientate the cup implant correctly relative to the natural bone and soft tissue structures. The cup implant is usually orientated in the acetabulum either using the cup impaction shaft as a guide or by using an external alignment guide attached to the impaction shaft. Examples of external alignment guides generally include two rods perpendicular to one another. The inclination angle of the cup is set by placing one of these rods parallel to the transverse axis of the patient and the anteversion angle is set by placing the other parallel to the longitudinal axis of the patient. However, despite all care having been taken, the orientation of the cup in the replaced hip can deviate from the ideal. This may be due to one or more factors. First the positioning of the cup is judged by aligning the introducer shaft or alignment rods by eye and as the orientation to be judged is a compound angle, it is difficult to visualise. Second as the rim the acetabulum is not uniform and, in the case of osteoarthritic hip, may be distorted by osteophytes, the acetabular rim is not generally a reliable guide for orientating the cup implant. A third problem is that alignment guides usually rely on the pelvis being in a known position which may itself be difficult to judge particularly with obese patients or patients who are not correctly positioned on the operating table. A fourth problem is that alignment guides are usually set to fixed angles of inclination and anteversion. This is generally acceptable for the majority of patients, however there is a wide range of anteversion within the anatomy of the normal population, meaning that in some circumstances the surgeon may wish to vary anteversion according to the natural anatomy of the patient. In view of these difficulties, the cup may sometimes be located as much as 20 degrees from the optimum intended angles.

Patient specific instruments (PSI) are sometimes used in joint replacement operations to help position implants. They are defined and constructed preoperatively based on three-dimensional digital images of the patient's joints. The digital models of the patient's joint can be reconstructed from medical scans of the patient using commercially available CAD (Computer Aided Design) and/or other specific planning software. The surgeon or skilled technician interacts with the software to place the joint implants in the desired positions relative to the patient's scanned bones. A patient matched guide is then defined and constructed using rapid prototyping techniques such as additive manufacture. These guides are devised to fit exactly to exposed bone surfaces intraoperatively so that the joint implants can be directed exactly to their planned positions.

The advantage of using PSI cup guides for positioning hip cups has not been proven compared to conventional guides and, as a result, they are seldom used. This is mainly due to the limited access to bone surfaces in the acetabulum for successful registration of a PSI guide. Typically, when a surgeon prepares the surgical exposure to the hip, access to the acetabulum is just sufficient to fit the cup implant in, therefore a PSI guide which is any bigger than the appropriately sized cup implant will be difficult to fit in unless the surgical exposure is extended. Furthermore, the acetabular socket is lined with articular cartilage, so it is difficult to gain accurate registration via the socket unless portions of the cartilage are removed. Removing cartilage from the acetabular is a very difficult and painstaking process which surgeons are opposed to doing. The acetabular rim is also partially covered in soft tissue (the acetabular labrum), however this being more exposed and softer, it is easier to remove by excision with a scalpel or electrocautery device, revealing the underlying bone surface at the acetabular rim. Just outboard of the labrum are joint capsule attachments, so, once the labrum is excised, only a very narrow portion of the acetabular rim is available for registration of a PSI guide.

Given that the best opportunity for registering a PSI guide is via a narrow portion of the acetabular rim, it is much easier to successfully register an acetabular guide at an early stage (before reaming the acetabulum) because the thin section of rim will be fully preserved. However, it is then necessary to capture the registered position until a later stage of the operation, so that the cup implant can be placed in an identical orientation as the guide after reaming the acetabulum. If registration is attempted after reaming the acetabulum, it's likely that some or all the narrow portion of the rim which is ideal for registration will have been removed during the reaming process.

STATEMENT OF INVENTION

To address these difficulties, the present invention is an acetabular cup guide which can be reduced in size to fit it into the acetabular socket through a minimal surgical exposure. Once inside the socket, the guide expands outwards to a fixed position to register the bone surfaces of the acetabular rim. In the context of the invention, the word "proximal" is used to refer to a part of the guide which is closer to the patient's acetabulum during use, and the word "distal" is used to refer to a part of the guide which is further away from the patient's acetabulum during use.

In a first aspect, the present invention relates to an acetabular cup guide comprising:
  (a) a distal end which is shaped to allow removable connection to a surgical instrument,
  (b) a proximal end comprising one or more contact surfaces which are shaped to conform to an acetabulum, and
  (c) a central proximal-distal axis extending through the acetabular cup guide,
wherein at least one of the one or more contact surfaces is deflectable towards the central proximal-distal axis in order to reduce an axial cross-section of the acetabular cup guide. In particular, the distal end may be shaped to allow removable connection to an impaction shaft.

More particularly, the one or more contact surfaces may comprise at least one fixed contact surface. Even more particularly, the one or more contact surfaces may comprise at least one fixed contact surface and at least two deflectable contact surfaces, more particularly at least three deflectable contact surfaces.

In particular, at least one of the one or more contact surfaces may be provided with one or more protrusions for engaging the cartilage in the acetabulum. More particularly, the one or more protrusions may be cone-shaped and taper as they extend away from the contact surface. In particular, the one or more contact surfaces may comprise at least one fixed contact surface and the one or more protrusions may be provided on the fixed contact surface. More particularly, the one or more protrusions may be fin-shaped, and in particular may be provided on one or more of the deflectable contact surfaces.

In particular, the one or more deflectable contact surfaces may comprise at a proximal end a resiliently deflectable hinge section. More particularly, the resiliently deflectable hinge section may extend substantially perpendicularly to the central proximal-distal axis.

More particularly, the one or more deflectable contact surfaces may comprise at a distal end a lip which is shaped to conform to an acetabular rim. Even more particularly, the lip may extend substantially perpendicularly to the central proximal-distal axis.

In particular, the one or more deflectable contact surfaces may comprise an inner surface which, in use, does not contact the acetabulum and which is provided with opposing jaws each with a jaw protrusion which engages opposing slots on a tab extending substantially perpendicularly to the central proximal-distal axis. More particularly, the opposing slots may comprise a distal stop which each jaw protrusion abuts when the one or more deflectable contact surfaces are in a non-deflected position, the opposing slots extending towards the central proximal-distal axis in a proximal direction in order to allow the one or more deflectable contact surfaces to deflect towards the central proximal-distal axis.

In an alternative embodiment, the one or more deflectable contact surfaces may comprise an inner surface which, in use, does not contact the acetabulum and which is provided with a hinged connection to a point on the central proximal-distal axis in order to allow the one or more deflectable contact surfaces to deflect towards the central proximal-distal axis.

More particularly, the one or more deflectable contact surfaces may be connected to a central post which is co-axial with the central proximal-distal axis and which is slidable within a through hole in the acetabular cup guide in order to allow the one or more deflectable contact surfaces to deflect towards the central proximal-distal axis. Even more particularly, the central post may comprise a lockable member which releasably holds the one or more deflectable contact surfaces in a deflected position.

In particular, the acetabular cup guide may be a patient specific instrument. More particularly, the one or more contact surfaces may comprise at least one fixed contact surface, one or more protrusions are provided on the fixed contact surface, and the acetabular cup guide is shaped such that the protrusions engage a specific patient's acetabular notch and transverse ligament.

In a second aspect, the present invention relates to a method of inserting an acetabular cup guide as described above into an acetabulum, the method comprising the steps of:
  (a) releasably connecting the distal end of the acetabular cup guide to an insertion tool,
  (b) deflecting the at least one of the one or more deflectable contact surfaces of the acetabular cup guide towards its central proximal-distal axis, and
  (c) inserting the acetabular cup guide into the acetabulum such that the one or more deflectable contact surfaces deflect away from the central proximal-distal axis and towards the acetabulum, In a third aspect, the present invention relates to a method of positioning a surgical instrument for orthopaedic surgery, the method comprising steps (a)-(c) of the method described above of inserting an acetabular cup guide, and additionally comprising the steps of:
  (d) placing a first proximal end of a lockable arm on a previously inserted ischium pin,
  (e) aligning a second distal end of the lockable arm with the insertion tool in order to record the position of the insertion tool with the lockable arm.

In a fourth aspect, the present invention relates to a method of implanting an acetabular cup implant into an acetabulum, the method comprising steps (a)-(e) of the method described above of positioning a surgical instrument for orthopaedic surgery, and additionally comprising the steps of:
  (f) removing the lockable arm from the ischium pin,
  (g) reaming the acetabulum,
  (h) placing the lockable arm back onto the ischium pin in position recorded in step (e),
  (i) releasably connecting the acetabular cup implant to an insertion tool,
  (j) inserting the acetabular cup implant into the acetabulum using the insertion tool aligned by the lockable arm, and
  (k) detaching the insertion tool from the acetabular cup implant.

In a fifth aspect, the present invention relates to a computer-readable medium having computer-executable instructions adapted to cause a 3D printer to print an acetabular cup guide as described above.

DETAILED DESCRIPTION

The guide is compressible in size, so that when the surgical exposure to the acetabulum is just sufficient to fit the cup implant in, the compressed guide will fit easily pass through the soft tissue and into the acetabular socket. The guide may be attached to an impaction shaft and inserted into the acetabular socket via the shaft. Once inside the socket, the guide is expandable by pressing the shaft towards the socket. During expansion, one or several portions of the cup guide extend outwards, preferably to a fixed position, to register on the bone surfaces of the acetabular rim. When fully extended, the acetabular guide may become rigid, so it behaves like a single mono-block rigid part, registering several portions of the acetabular rim simultaneously. The result is that the guide and attached shaft can achieve stability in the intended planned position. In a particularly embodiment, the guide only expands and locks out fully in the intended position, and thus it provides tactile feedback that the planned position has been located. The present invention includes a method to capture the registered position, so that the position can be transferred to the cup implant at a later stage of the operation. When the cup guide is removed from the socket, it can be compressed in size so that it can easily be removed through an exposure just sufficient to fit the cup implant in. Those skilled in the art will appreciate there are several methods of compressing and expanding a hemispherical shaped guide to make it fit within a hemispherical acetabular socket without overhanging the rim.

Examples of the invention will now be described by referencing the accompanying drawings, which are not intended to limit the scope of the invention claimed, in which:

A preferred embodiment of the PSI cup guide is shown in FIGS. 1-7. An alternative embodiment is shown in FIGS. 8-12. FIGS. 13-19 show the preferred embodiment in use with the pelvic bone, impaction shaft and Ischium pin imbedded in the pelvic bone.

In FIGS. 1-4 it can be seen that this embodiment of the PSI acetabular guide comprises an outer part [1] and an inner part [2]. The outer part [1] consisting of a central hub [3], a base [4] and a multitude of movable petals [5] (for example 3 petals, ie the deflectable contact surfaces). Each petal is connected to the base [4] by a thin section forming a deflectable hinge [6]. Each petal [5] includes an overhanging portion [7] (ie a lip) intended to engage with the bone surfaces of the acetabular rim. Each petal [5] also includes one or more fins [8] which engage with the inner cartilage covered surface of the acetabulum. Base [4] includes a multitude of spikes [9] (for example 3 spikes) which press though soft tissue and engage with the bone surface in the acetabular fossa.

Figure 1:
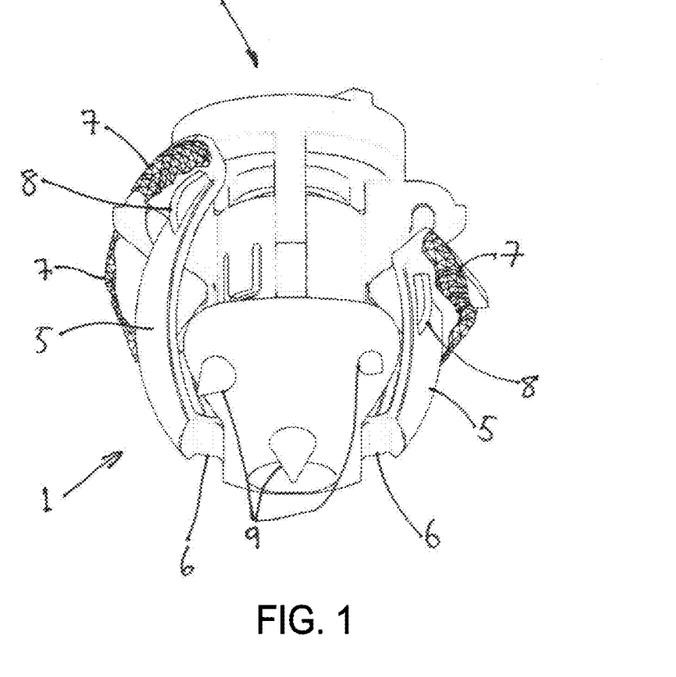
FIG. 1 shows the assembled PSI cup guide according to one embodiment of the invention in the compressed state.
Figure 2:
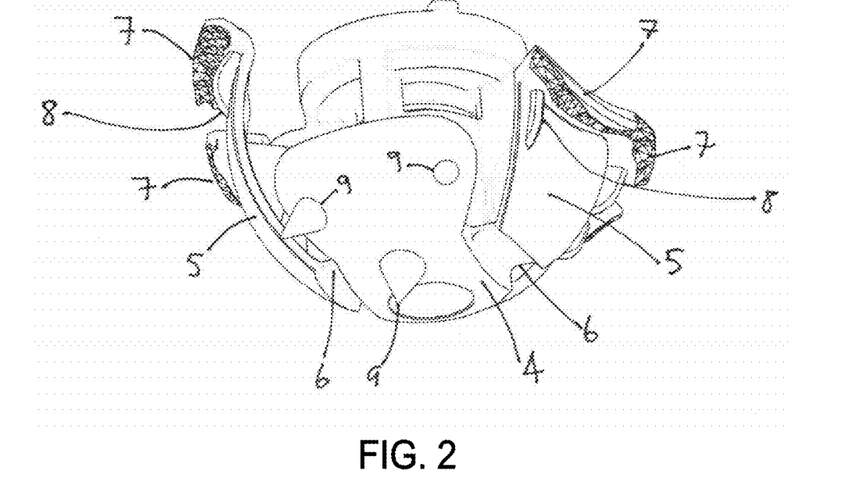
FIG. 2 shows the assembled PSI cup guide of FIG. 1 in the expanded state.
Figure 3:
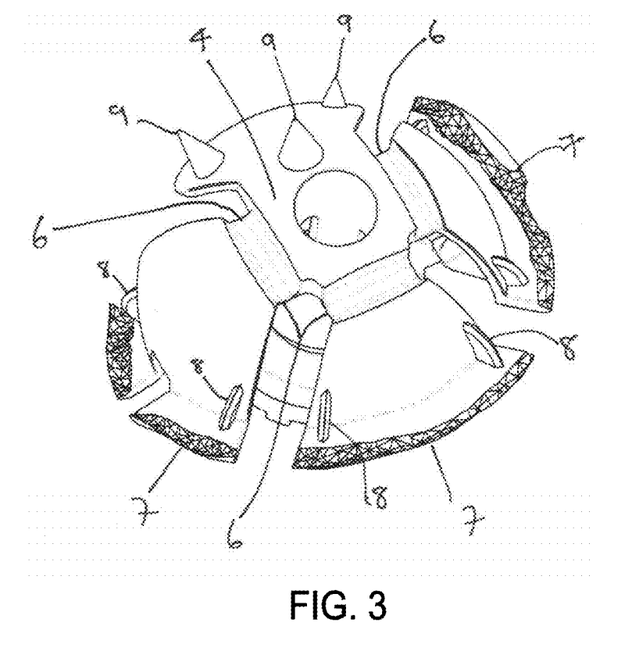
FIG. 3 is another view of the assembled PSI cup guide of FIG. 1 in the expanded state.
Figure 4:
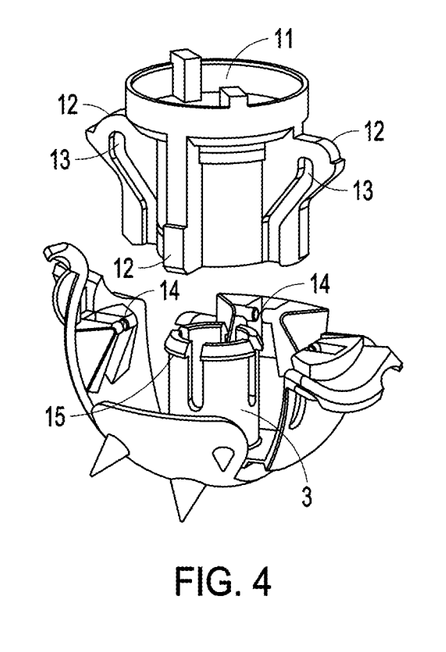
FIG. 4 is an exploded view of the PSI cup guide of FIG. 1 showing a two-part assembly.

As shown in FIG. 4, the inner part [2] consisting of a central boss [10] with an aperture [11] and a multitude of tabs or webs [12] (for example 3 webs) extending outwards and incorporating slots [13] on both sides.

In FIG. 4 on the outer part [1], protrusions [14] are visible, which engage in slots [13] on the inner part [2] when assembled together.

Figure 5:
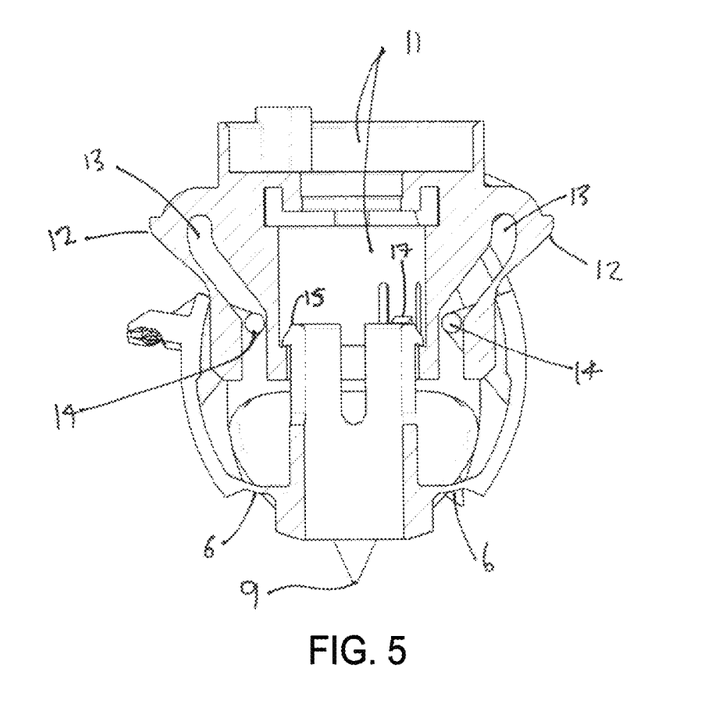
FIG. 5 is a cross section view of the PSI cup guide of FIG. 1 in the compressed state.
Figure 6:
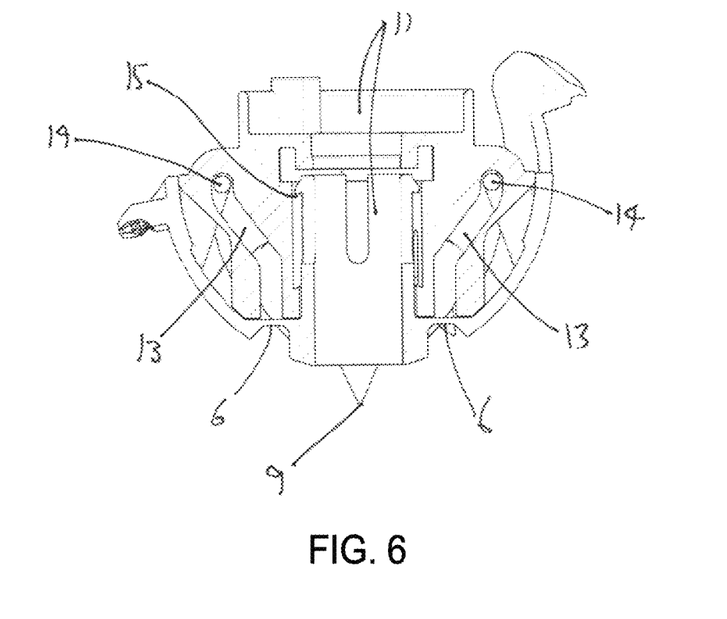
FIG. 6 is a cross section view of the PSI cup guide of FIG. 1 in the expanded state.
Figure 7:
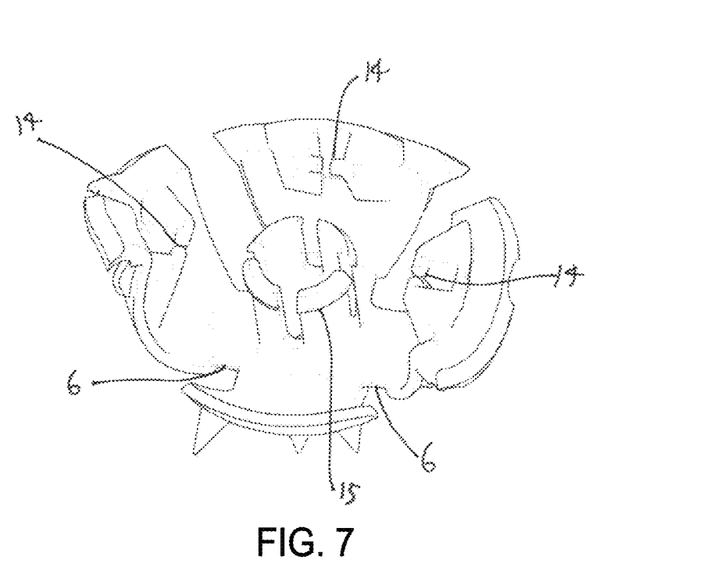
FIG. 7 shows the outer part of the cup guide of FIG. 1 separately.
Figure 8:
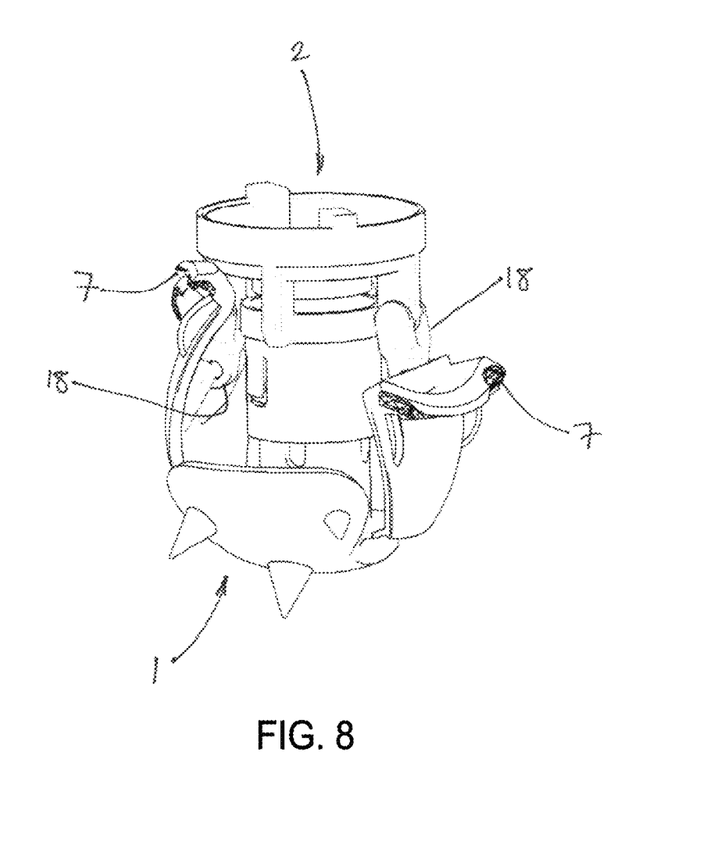
FIG. 8 is an alternative embodiment of the PSI cup guide with a different mechanism to expand and contract the guide, shown in the compressed state.
Figure 9:
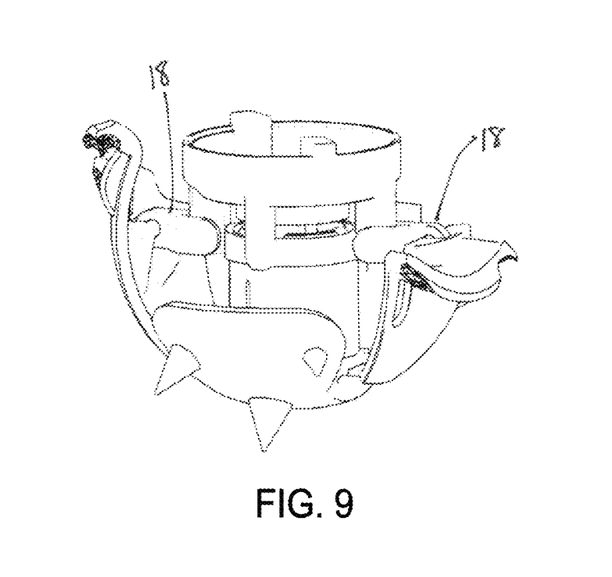
FIG. 9 shows the PSI cup guide of FIG. 8 in the expanded state.
Figure 10:
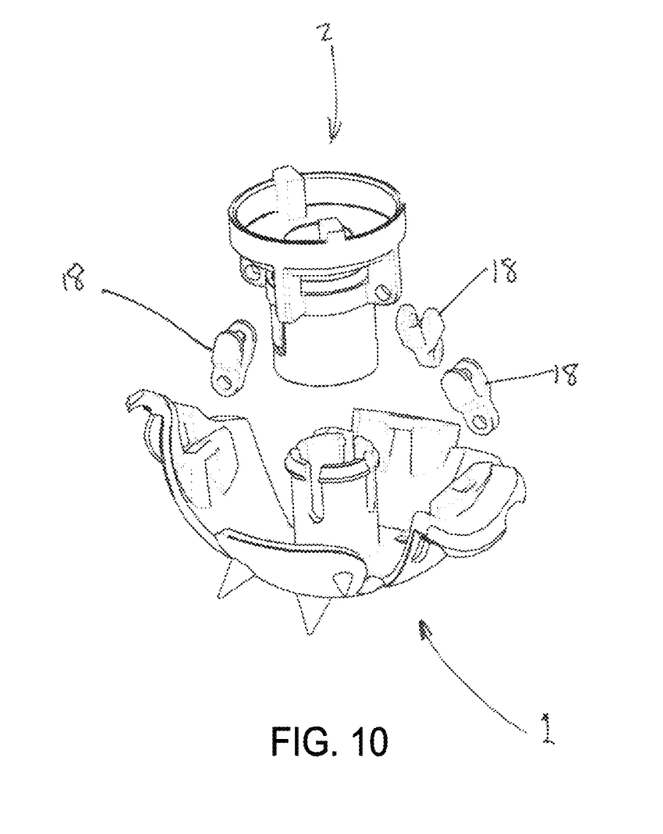
FIG. 10 is an exploded view of the PSI cup guide of FIG. 8 showing a 5-part assembly.
Figure 11:
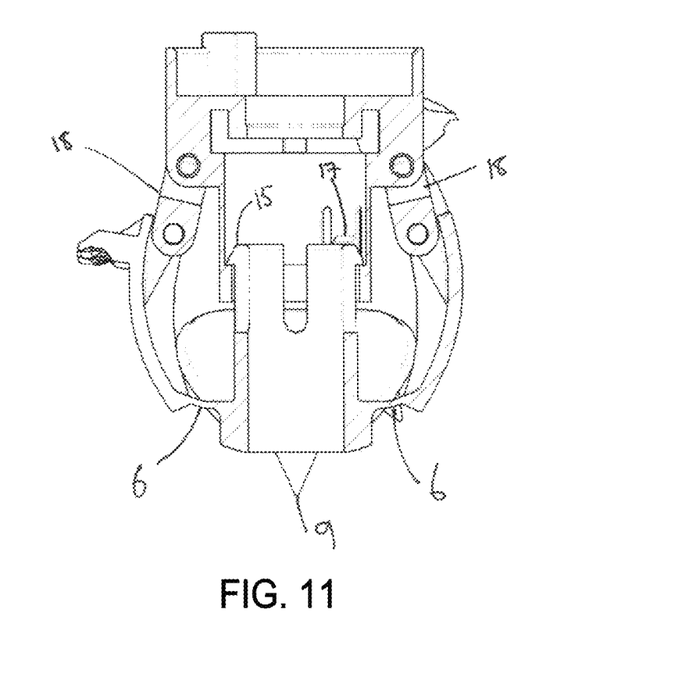
FIG. 11 is a cross section view of the PSI cup guide of FIG. 8 in the compressed state.

In FIGS. 5 and 6 it can be seen that the two parts of the acetabular guide [1 and 2] are held together by a resiliently deflectable latch [15] (ie a lockable member). This latch deflects inwards to enable assembly of the two parts and retains them together in use. Inner part [2] can slide in relation to outer part [1] in a proximal distal axis from high to low position. Protrusions [14] are engaged in slots [13] and the slots control the position of the petals [5] on outer part [1] relative to inner part [2]. When inner part [2] is at its highest position the petals are deflected inwards towards the central axis, as in FIG. 5 and when inner part [2] is at its lowest position the petals [5] are deflected outwards away from the central axis, as in FIG. 6. Aperture [11] provides a connection with the impaction shaft [16] shown in later figures. Also, visible in FIG. 5 is protrusion [17] which temporarily holds inner part [2] in the highest position, as in FIG. 5. In FIG. 7 outer part [1] is shown in isolation to further define the features above.

Figure 12:
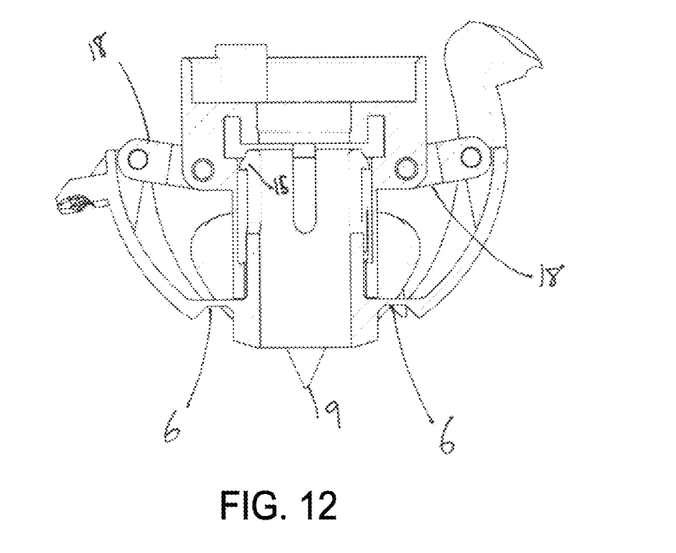
FIG. 12 is a cross section view of the PSI cup guide of FIG. 8 in the expanded state.

An alternative embodiment is shown in FIGS. 8-12. This embodiment is identical to that shown in FIGS. 1-7 except that linkages [18] provide alternative connections (instead of slots [13] and protrusions [14]) between the movable petals [5] and inner part [2]. These linkages (or hinges) control the position of the petals [5] on outer part [1] relative to inner part [2]. When inner part [2] is at its highest position the petals [5] are deflected inwards towards the central axis as in FIGS. 8 and 11 and when inner part [2] is at its lowest position the petals [5] are deflected outwards away from the central axis, as in FIGS. 9 and 12. In FIG. 12 it can also be seen how the linkage [18] pivot points are positioned to achieve an over-centre bias when the petals [5] are pressed to their fully expanded position in the acetabular socket.

The in-use function of the patent specific acetabular guide will now be described with reference to FIGS. 13-19.

Figure 13:
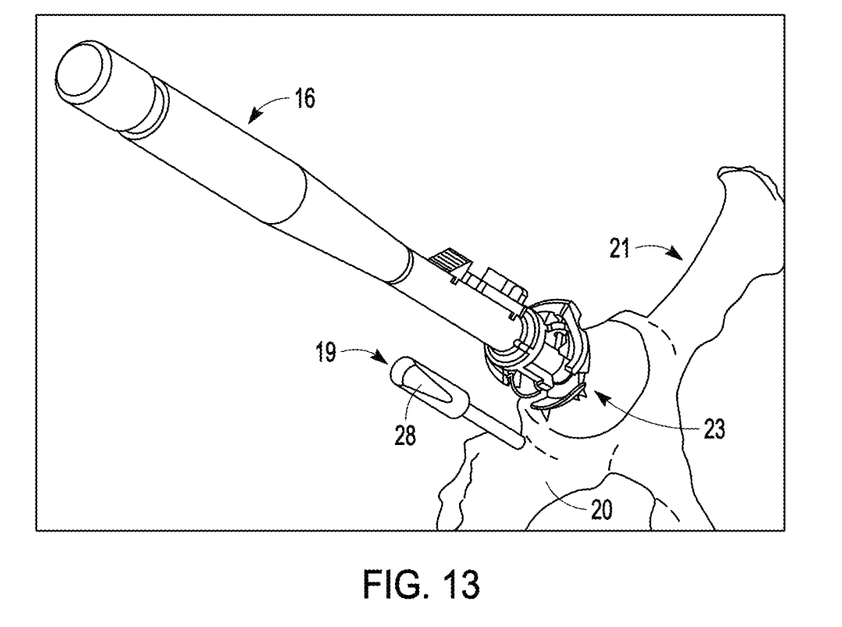
FIG. 13 is a view of the acetabular cup guide of FIG. 1 being inserted into the acetabulum via an impaction shaft, also showing the ischium pin embedded in the pelvic bone.

In FIG. 13, the ischium pin [19] is shown pre-inserted in the Ischium bone [20] of the pelvis [21]. This type of pin is often used in hip replacement as a capsule retractor. In this case the ischium pin [19] is also used as a connection for the lockable arm [22] shown in later figures. It is therefore important that the pin is stable in the ischium bone and doesn't wobble or rotate. In FIG. 13 the acetabular guide in its compressed state is being inserted into the acetabulum [23]. The soft tissue and surgical access is not shown, so it is not apparent that the surgical access is usually just of sufficient size to fit the cup implant in.

Figure 14:
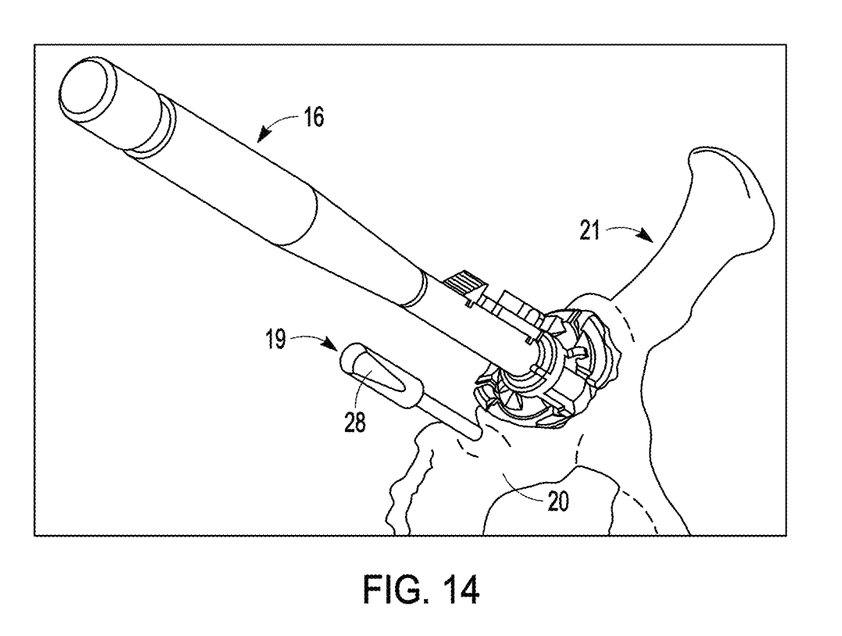
FIG. 14 is a view of the acetabular cup guide of FIG. 1 following expansion in the acetabulum by pressing the impaction shaft.

In FIG. 14, the acetabular guide has been expanded, by pushing the Impaction shaft [16] towards the acetabular socket. When the guide registers against the bone surface of the acetabular rim in its intended (planned) position, it will be fully expanded and will feel stable, because the guide contact surfaces exactly match the profile of the bone surfaces on the acetabular rim [25]. When successfully registered, the impaction shaft [16] will be precisely orientated to place the cup implant [26] in the planned position. However, because the cup implant is inserted at a later stage (after reaming the acetabulum) this position must be captured now and later transferred to the cup implant which is inserted with the same impaction shaft.

Figure 15:
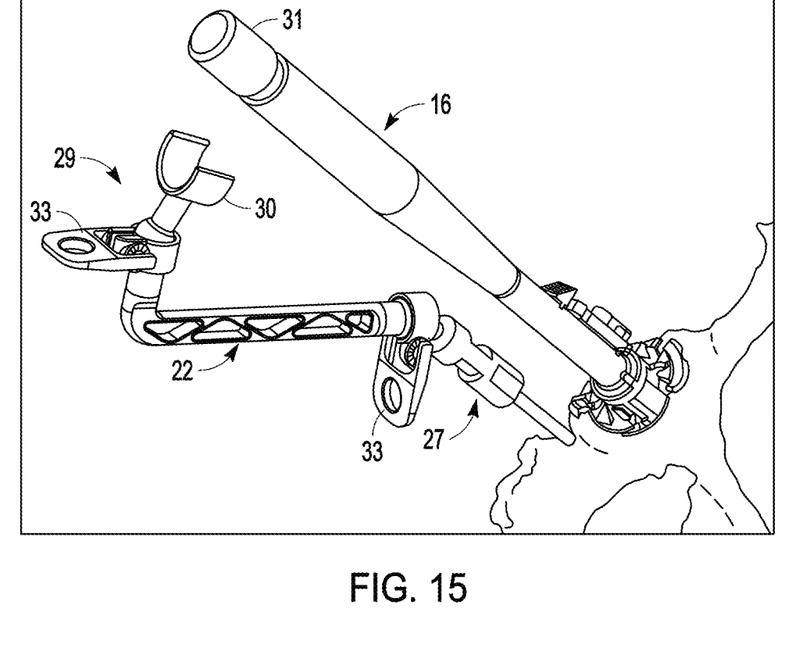
FIG. 15 is a view of the guide of FIG. 1 in the registered position with introduction of a lockable arm mounted on the Ischium pin.

In FIG. 15, the lockable arm [22] is assembled onto the ischium pin [19]. The connection [27] between lockable arm and ischium pin incorporates a close-fitting diameter and tapered flat [28], to ensure that a single distinct position is located without any free-play (ie the lockable arm cannot rotate on the ischium pin). Thus, ensuring that the lockable arm [22] can be removed, set aside and relocated on the ischium pin [19] in the exact same position later.

Figure 16:
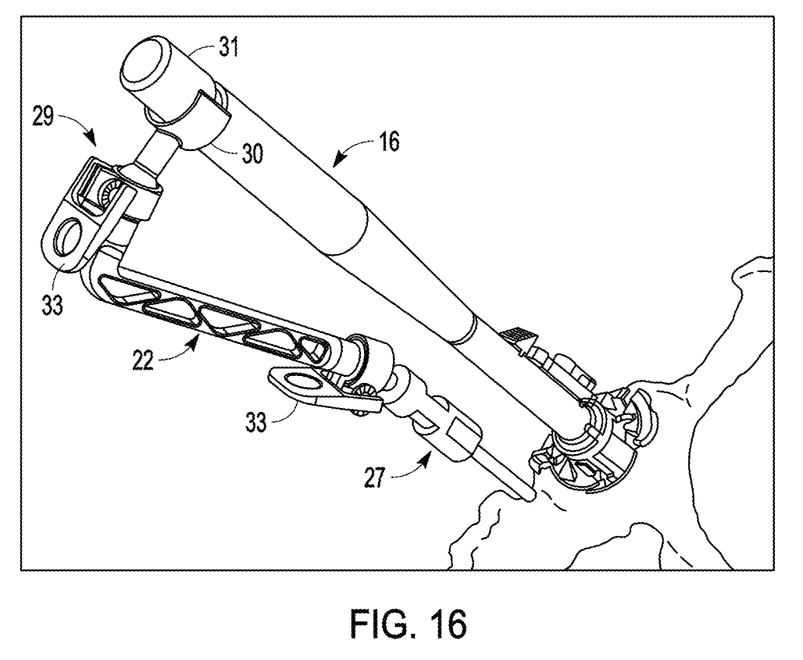
FIG. 16 is a view of the guide of FIG. 1 in the registered position with the lockable arm yoke moved into position on the shaft.

In FIG. 16 the distal end [29] of the lockable arm [22] is moved to a position where the yoke connector [30] locates onto the distal end [31] of the impaction shaft [16]. At the same time the impaction shaft [16] is pressed towards the acetabulum to ensure the registered position is maintained. The lockable arm [22] incorporates two ball-in-socket joints [32], allowing the yoke [30] to be manipulated to precisely fit with the distal end [31] of the impaction shaft [16]. Both ball-in-socket joints [32] can be locked in any position by actuating the locking levers [33]. In this figure the lockable arm [22] has been locked, capturing the position of the distal impaction shaft.

Figure 17:
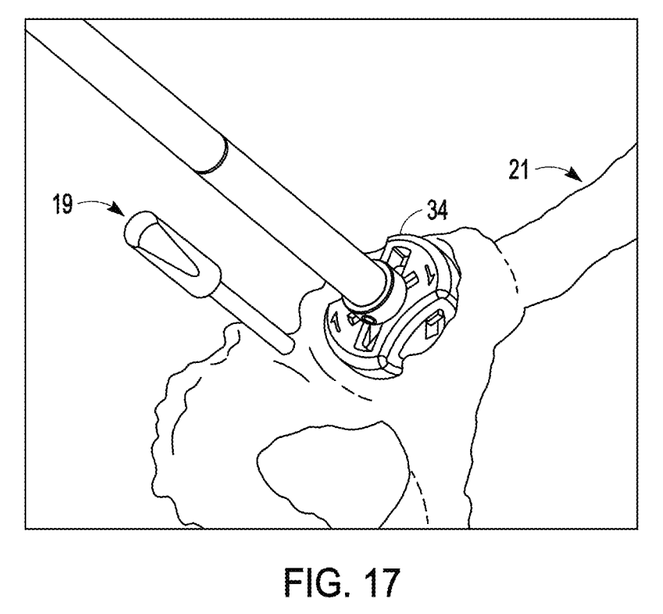
FIG. 17 shows reaming of the acetabulum using a standard technique (the PSI guide and lockable arm have been removed)

In FIG. 17 the acetabular guide and impaction shaft have been removed and the lockable arm removed and set aside for later use. The acetabulum is being reamed with a standard technique with hemispherical reamers [34] to provide the appropriate fit of the cup implant.

Figure 18:
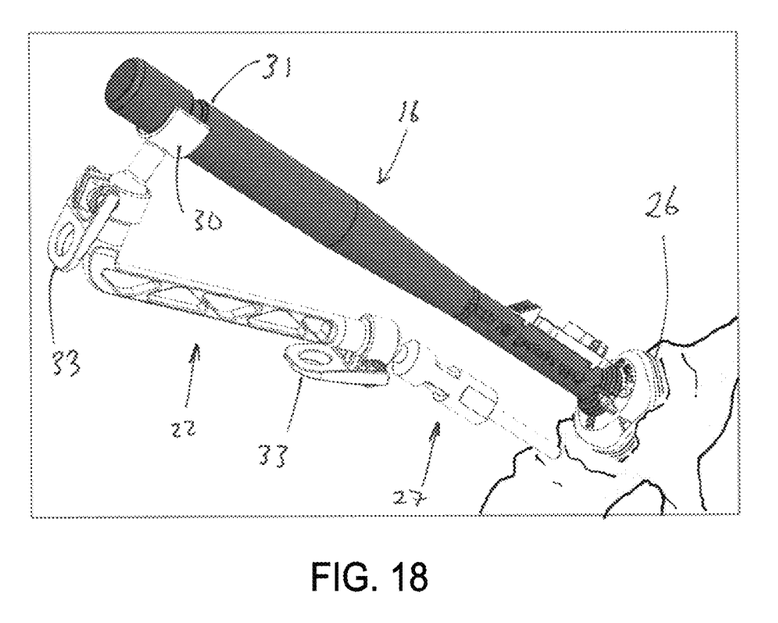
FIG. 18 is a view of the cup implant being inserted into the acetabular socket via the Impaction shaft whilst being guided by the lockable arm.

In FIG. 18 the lockable arm [22] has been replaced onto the ischium pin [19] and the cup implant [26] is now attached to the impaction shaft [16]. The distal end [31] of the impaction shaft [16] should now take up an identical position provided it is positioned in the yoke [30] of the lockable arm [22]. With the impaction shaft [16] in position in the yoke [30], the cup implant [26] is carefully impacted into the acetabulum. It is very important that the ischium pin [19] does not move, and the lockable arm [16] is not further adjusted between initial registration and final positioning of the cup implant [26], otherwise the registered position will be lost.

Figure 19:
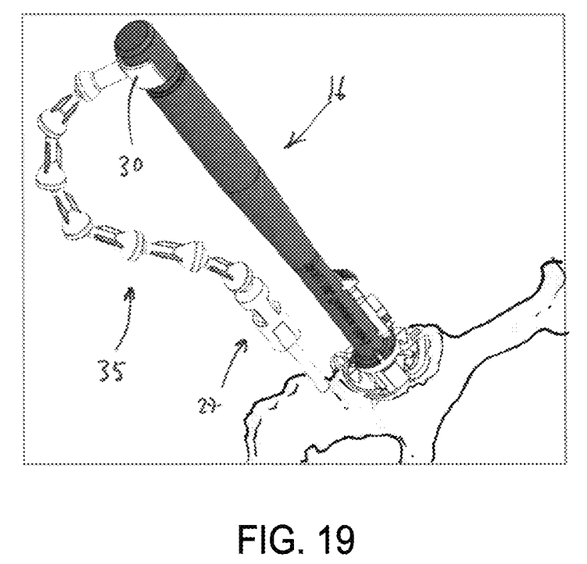
FIG. 19 shows the PSI cup guide of FIG. 1 with an alternative semi-rigid arm.

In FIG. 19, an alternative semi rigid arm [35] is shown. In this case the arm is positioned in the same way, but instead of a locking mechanism, the arm [35] maintains its position due to the frictional resistance between the multitude of ball joints [36].

Following impaction of the cup implant, the ischium pin [27] is removed from the pelvic bone.

The invention claimed is:

1. An acetabular cup guide comprising:
   (a) a distal end which is shaped to allow removable connection to a surgical instrument,
   (b) a proximal end comprising one or more contact surfaces which are shaped to conform to an acetabulum, and
   (c) a central proximal-distal axis extending through the acetabular cup guide,
   wherein at least one of the one or more contact surfaces is deflectable towards the central proximal-distal axis in order to reduce an axial cross-section of the acetabular cup guide,
   wherein the one or more deflectable contact surfaces comprise at a proximal end a resiliently deflectable hinge section, and
   wherein at least one of the one or more contact surfaces is provided with one or more protrusions for engaging the cartilage in the acetabulum.

2. An acetabular cup guide as claimed in claim 1, wherein the distal end is shaped to allow removable connection to an impaction shaft.

3. An acetabular cup guide as claimed in claim 1, wherein the one or more contact surfaces comprise at least one fixed contact surface.

4. An acetabular cup guide as claimed in claim 3, wherein the one or more contact surfaces comprise at least one fixed contact surface and at least three deflectable contact surfaces.

5. An acetabular cup guide as claimed in claim 1, wherein the one or more protrusions are cone-shaped and taper as they extend away from the contact surface.

6. An acetabular cup guide as claimed in claim 1, wherein the one or more contact surfaces comprise at least one fixed contact surface and the one or more protrusions are provided on the fixed contact surface.

7. An acetabular cup guide as claimed in claim 1, wherein the resiliently deflectable hinge section extends substantially perpendicularly to the central proximal-distal axis.

8. An acetabular cup guide as claimed in claim 1, wherein the one or more deflectable contact surfaces comprise at a distal end a lip which is shaped to conform to an acetabular rim.

9. An acetabular cup guide as claimed in claim 8, wherein the lip extends substantially perpendicularly to the central proximal-distal axis.

10. An acetabular cup guide as claimed in claim 1, wherein the one or more deflectable contact surfaces comprise an inner surface which, in use, does not contact the acetabulum and which is provided with opposing protrusions which engage opposing slots on a tab extending substantially perpendicularly to the central proximal-distal axis.

11. An acetabular cup guide as claimed in claim 10, wherein the one or more deflectable contact surfaces comprise an inner surface which, in use, does not contact the acetabulum and which is provided with a hinged connection to a central hub in order to allow the one or more deflectable contact surfaces to deflect towards the central proximal-distal axis.

12. An acetabular cup guide as claimed in claim 10, wherein the one or more deflectable contact surfaces are connected to a central hub, each of the one or more deflectable contact surfaces including opposing protrusions that engage opposing slots in the central hub.

13. An acetabular cup guide as claimed in claim 12, wherein the central hub comprises a lockable member which releasably holds the one or more deflectable contact surfaces in a deflected position.

14. An acetabular cup guide as claimed in claim 10, wherein the acetabular cup guide is a patient specific instrument.

15. An acetabular cup guide as claimed in claim 14, wherein the one or more contact surfaces comprise at least one fixed contact surface, one or more protrusions are provided on the fixed contact surface, and the acetabular cup guide is shaped such that the protrusions engage a specific patient's acetabular notch and transverse ligament.

16. A method of inserting an acetabular cup guide into an acetabulum, the method comprising:
   releasably connecting a distal end of the acetabular cup guide to an insertion tool, the acetabular cup guide including one or more deflectable contact surfaces at a proximal end, the one or more deflectable contact surfaces including a resiliently deflectable hinge section;
   deflecting at least one of the one or more deflectable contact surfaces of the acetabular cup guide towards a central proximal-distal axis of the acetabular cup guide; and
   inserting the acetabular cup guide into the acetabulum such that the one or more deflectable contact surfaces deflect away from the central proximal-distal axis and engage soft tissue in the acetabulum.

17. An acetabular cup guide comprising:

(a) a distal end which is shaped to allow removable connection to a surgical instrument,
(b) a proximal end comprising one or more contact surfaces which are shaped to conform to an acetabulum, and
(c) a central proximal-distal axis extending through the acetabular cup guide, wherein at least one of the one or more contact surfaces is deflectable towards the central proximal-distal axis in order to reduce an axial cross-section of the acetabular cup guide, and wherein the at least one of the one or more deflectable contact surfaces comprises an inner surface which, in use, does not contact the acetabulum and which is provided with opposing protrusions which engage opposing slots on a tab extending substantially perpendicularly to the central proximal-distal axis.

* * * * *

UNITED STATES PATENT AND TRADEMARK OFFICE
CERTIFICATE OF CORRECTION

PATENT NO. : 11,382,767 B2
APPLICATION NO. : 16/763868
DATED : July 12, 2022
INVENTOR(S) : Robert Michael Wozencroft It is certified that error appears in the above-identified patent and that said Letters Patent is hereby corrected as shown below:

On the Title Page

In Column 2, under "Other Publications", Line 2, delete "dataed" and insert --dated-- therefor In the Claims In Column 8, Line 26, in Claim 11, delete "claim 10," and insert --claim 1,-- therefor In Column 8, Line 33, in Claim 12, delete "claim 10," and insert --claim 1,-- therefor In Column 8, Line 42, in Claim 14, delete "claim 10," and insert --claim 1,-- therefor Signed and Sealed this
Fourth Day of October, 2022

Katherine Kelly Vidal
*Director of the United States Patent and Trademark Office*